US010414681B2

(12) United States Patent
Nilsen et al.

(10) Patent No.: US 10,414,681 B2
(45) Date of Patent: Sep. 17, 2019

(54) METHOD FOR RECOVERY OF PHOSPHATE

(71) Applicant: Cambi Technology AS, Asker (NO)

(72) Inventors: Paal Jahre Nilsen, Bødalen (NO); Hans Rasmus Holte, Reistad (NO)

(73) Assignee: CAMBI TECHNOLOGY AS, Asker (NO)

( * ) Notice: Subject to any disclaimer, the term of this patent is extended or adjusted under 35 U.S.C. 154(b) by 0 days.

(21) Appl. No.: 16/099,627

(22) PCT Filed: May 19, 2017

(86) PCT No.: PCT/EP2017/062142
§ 371 (c)(1),
(2) Date: Nov. 7, 2018

(87) PCT Pub. No.: WO2017/198834
PCT Pub. Date: Nov. 23, 2017

(65) Prior Publication Data
US 2019/0144320 A1 May 16, 2019

(30) Foreign Application Priority Data
May 20, 2016 (EP) .................... 16170684

(51) Int. Cl.
C02F 11/04 (2006.01)
C02F 11/14 (2019.01)
(Continued)

(52) U.S. Cl.
CPC ............ *C02F 11/04* (2013.01); *C02F 11/121* (2013.01); *C02F 11/14* (2013.01); *C02F 11/18* (2013.01);
(Continued)

(58) Field of Classification Search
CPC ......... C02F 11/04; C02F 11/121; C02F 11/18; C02F 11/14; C02F 2101/105;
(Continued)

(56) References Cited

U.S. PATENT DOCUMENTS

2010/0021979 A1 1/2010 Facey et al.
2014/0374348 A1* 12/2014 Ewert .................. C02F 3/1215
210/631
2015/0275234 A1* 10/2015 Ketola .................. C12P 5/023
435/167

FOREIGN PATENT DOCUMENTS

WO WO 2013/133703 A1 9/2013

OTHER PUBLICATIONS

International Preliminary Report on Patentability for Appl. No. PCT/EP2017/062142 dated May 17, 2018.
(Continued)

*Primary Examiner* — Fred Prince
(74) *Attorney, Agent, or Firm* — Birch, Stewart, Kolasch & Birch, LLP

(57) ABSTRACT

The present invention provides a method for recovery of phosphate, in the form of magnesium ammonium phosphate (MAP), from a process for treating a biomass material which process comprises a digestion step performed in a digestion tank and includes a pre-treatment step employing a thermal hydrolysis, characterized in that a magnesium source is added to the material in the process flow before said flow enters the digestion tank, and phosphate is recovered as MAP as an integral part of a solid or semi-solid digestate product from the digestion tank.

15 Claims, 3 Drawing Sheets

(51) Int. Cl.
*C02F 11/12* (2019.01)
*C02F 11/18* (2006.01)
*C01B 25/45* (2006.01)
*C12M 1/107* (2006.01)
*C12M 1/00* (2006.01)
*C02F 11/121* (2019.01)
*C02F 101/10* (2006.01)

(52) U.S. Cl.
CPC ............ *C12M 21/04* (2013.01); *C12M 45/06* (2013.01); *C01B 25/451* (2013.01); *C02F 2101/105* (2013.01); *C02F 2201/002* (2013.01); *C02F 2209/001* (2013.01); *C02F 2209/06* (2013.01)

(58) Field of Classification Search
CPC ............ C02F 2201/002; C02F 2209/06; C02F 2209/001; C12M 45/06; C12M 21/04; C01B 25/451
USPC ....... 210/603, 608, 609, 612, 613, 631, 259, 210/906, 907
See application file for complete search history.

(56) References Cited

OTHER PUBLICATIONS

International Search Report for PCT/EP2017/062142 (PCT/ISA/210) dated Aug. 2, 2017.
Written Opinion of the International Searching Authority for PCT/EP2017/062142 (PCT/ISA/237) dated Aug. 2, 2017.

* cited by examiner

METHOD FOR RECOVERY OF PHOSPHATE

FIELD OF THE INVENTION

The present invention relates to recovery of phosphate from the process flow of a process for treatment of material of primarily organic origin, e.g. in the form of waste or biomass. The phosphate is recovered as magnesium ammonium phosphate (MAP), or hydrates thereof, as an integral part of a solid or semi-solid digestate product.

BACKGROUND OF THE INVENTION

Municipal and industrial sludge and waste and other sources of waste-products of primarily organic origin such as by-products from gardening, agriculture, forestry, timber industry and the like, have over the years been the subject of increasing interest as possible starting materials for the production of e.g. $CO_2$-neutral fuels such as biogas or bioethanol.

Many known methods for production of $CO_2$-neutral fuels based on such organic waste or biomass include a pretreatment step employing some kind of Thermal Hydrolysis Process (THP) and an anaerobic digestion.

When organic waste or biomass is subjected to THP processes, this will in most cases result in a release of at least part of the otherwise organically bound phosphorus compounds. Thus, the material resulting from such processes will very often comprise relatively high concentrations of in particular orthophosphates. This is in particular true for THP-treated municipal and industrial sludge.

Thus, in addition to the desired $CO_2$-neutral fuels, these processes will after the anaerobic digestion result in solid, semi-solid and wastewater effluent fractions containing a considerable amount of phosphate originating from the source of organic material if no measures are taken to reduce the amount of phosphate in the course of the process. Various methods have previously been developed to recover some of the phosphate from the wastewater effluent in the form of pure magnesium ammonium phosphate (MAP) which is useful as fertilizer in the field of agriculture.

Known processes for recovery and precipitation of phosphate in the form of magnesium ammonium phosphate (MAP, $NH_4MgPO_4$, Struvite) from such processes include an addition of magnesium chloride to the solid or semi-solid fraction leaving the digestion tank wherein the anaerobic digestion is performed. These processes typically also encompass one or more separation steps where the solid or semi-solid waste are separated from the wastewater effluent prior to precipitating MAP from the then formed wastewater effluent fraction.

These processes, which are similar to methods for removal of phosphate applied also to different kinds of wastewater, have been known for some years, and are normally applied to the resulting waste product at the very end of the relevant procedure, e.g. to the product resulting from the treatment of the applicable biowaste in a digestion tank.

One such common method for recovering the phosphate in wastewater is by bringing the phosphate to react with ammonium already present in the wastewater and adding magnesium to form the precipitate $NH_4MgPO_4$.

EP1241140 describes a process called 'AirPrex' for the controlled formation and removal of struvite directly from digested sludge. In the AirPrex process the digested sludge is led through a reactor tank where air is supplied and magnesium is added as magnesium chloride ($MgCl_2$). Air is supplied in order to raise the pH value (by $CO_2$ stripping) and to obtain sufficient mixing of the sludge and the added magnesium chloride. The formed struvite is intermittently tapped from the (conical) reactor bottom. In a second tank, smaller crystals of struvite are allowed to settle.

The pH necessary for the precipitation of struvite (MAP), normally in the range of 7.6 to 8, is typically reached by the addition of alkaline agents, e.g. a sodium hydroxide solution or other alternative similar measures. Apart from the AirPrex process, several other alternative processes for recovery of struvite are known in the art.

US2012/0261334 discloses inhibition of formation of scale in a wastewater treatment system upstream of a struvite precipitation reactor by injection of $CO_2$. The injection may be controlled based on one or more of the variables pH, fluid flow and fluid pressure. The injected $CO_2$ may subsequently be stripped, at the precipitation reactor to enhance struvite production.

Another known alternative is the Crystalactor® technology, which was originally developed for water softening purposes. It was later recognized that the reactor could be used for the crystallization of a variety of (heavy metal) carbonates, phosphates, halides and sulfides in the process industry. Phosphate may be recovered in the form of struvite. In essence, the Crystalactor® is a cylindrical vessel which is partly filled with a suitable seed material. Feed, reagent and recirculating solution are pumped upward through the particle bed at a rate to maintain favorable mixing and supersaturation conditions. Effluent overflows the top of the reactor whereas the seed material in the bed grow into pellets through crystallization. As the pellets become progressively heavier they gradually move towards the bottom of the bed. Periodically, the lower portion of the bed is discharged into a pellet container and fresh seed material is added without interrupting the operation.

U.S. Pat. No. 8,445,259 discloses an apparatus and a method for treating organic sludge, wherein the sludge is first dewatered; the dewatered sludge is passed through a thermal hydrolysis reactor to hydrolyze polymers contained in the dewatered sludge; the hydrolyzed sludge is passed through a digester to digest the hydrolyzed sludge anaerobically; the digested sludge is again dewatered to form a dewatered cake and a solution; and then the solution is passed through a crystallization reactor to crystallize and remove phosphorus and nitrogen in the solution. In the crystallization step is typically added magnesium and an alkaline solution.

EP 1 364 915 A1 discloses a method for reducing phosphate from the liquid phase of digested sewage sludge, wherein wastewater is fed to aerobic treatment after the anaerobic treatment and sludge recycled from a settling tank is subjected to anaerobic treatment. The water fraction from a second solid/liquid separation step is then fed to an apparatus for removing phosphate, for example a MAP reactor.

WO 2009/112208 discloses a method for wastewater treatment and a wastewater treatment plant for this purpose, in which hydrolyzed and subsequently anaerobically treated sludge is fed to a separate precipitation unit in order to remove phosphate. In this method magnesium ammonium phosphate (MAP) is precipitated from the hydrolyzed and anaerobically treated sludge by addition of magnesium salts with the setting of a pH from 7.5 to 7.8.

In contrast to the above methods, WO 2013/034765 describes a method for separation of phosphate from a process flow, in which the separation is carried out after a thermal hydrolysis step but before the anaerobic digestion step, in the form of removal of Struvite (MAP) from the process flow by precipitation. A magnesium-containing precipitant is added to the process flow and a sub-quantity of the upstream anaerobically digested sludge in the form of a separated liquid phase is recirculated to the process flow after hydrolysis but before or during the step of removal of phosphate, to provide ammonium for formation of MAP. It is described that the removal of phosphate in the form of MAP crystals prior to the digestion step as compared to after the digestion step has the advantage that the ratio of crystal structure to sludge particle structure makes it possible to improve MAP crystal removal, for example by means of a centrifuge decanter, from the process flow, thus resulting in a higher MAP yield, with a relatively fine crystal structure. The process is described as being especially advantageous when the hydrolysis is performed at a temperature in the range of 70° to 90° C., and results in a hydrolyzed product with a pH in the range of 10 to 12.

Phosphorous is characterized as a limited resource on earth, relatively scarce and not evenly distributed around the planet. Today the phosphorous for fertilization comes from mining of phosphate rock as the guano reserves are depleted. Some researchers estimate that also the phosphate rock reserve will be depleted in 50-100 years. A large part of the until now mined phosphorous have ended up in the water environment or have been deposited with waste, thereby becoming unavailable for reuse. Recovery of phosphate becomes increasingly urgent.

Considering the increased need for effectively recovering phosphate from biomass products in general, including e.g. wastewater sludge, and municipal or industrial waste, there is a continued and increasingly urgent need for the development of efficient and energy saving methods for treating biomass and concomitantly recovering phosphate. For instance, there is a need for reducing the use of water, energy and costly chemical agents.

SUMMARY OF INVENTION

In a first aspect, the present invention relates to a method for recovery of phosphate from a process for treating biomass material comprising the steps of:
  i) adding a magnesium ion source to a biomass material;
  ii) subjecting the biomass material to a pre-treatment, comprising at least a step of:
    thermal hydrolysis at a temperature of 140-220° C., at saturation pressure;
  iii) transferring the pre-treated biomass material to a digestion tank and subjecting the pre-treated biomass material to an anaerobic digestion at a pH in a range of 7.5 to 8.5 thereby providing a digestate;
  iv) controlling the pH of the digestion tank by continuously removing biogas, including carbon dioxide and methane gas, and partially or fully separating the carbon dioxide from the biogas, and partially re-introducing the thereby obtained carbon dioxide reduced biogas to the digestion tank;
  v) optionally reducing the magnesium ammonium phosphate (MAP) concentration in the digestion tank by subjecting a sub quantity of the digestate to a MAP separation treatment and re-introducing any remaining solids or semi-solids into the digestion tank;
wherein steps i) and ii) are performed prior to step iii), and wherein the phosphate is recovered as magnesium ammonium phosphate (MAP), or hydrates thereof, as an integral part of a solid or semi-solid digestate product from the digestion tank.

In a second aspect, the present invention relates to the use of a solid or semi-solid digestate product from a method according to the present invention as soil conditioner and/or fertilizer.

In a third aspect, the present invention relates to a biomass treatment plant for production of biogas, said biomass treatment plant including:
  at least one biomass pre-treatment reactor (2) having an biomass material inlet for feeding untreated biomass material (1) and having a pre-treated biomass material outlet;
  at least one digestion tank (3) having a pre-treated biomass material inlet connected to said pre-treated biomass material outlet and having a biogas outlet (9) and at least one digestate product outlet (5) for the digestate product including as an integral part recovered magnesium ammonium phosphate (MAP);
  a carbon dioxide separation device (10) having a biogas inlet connected to said biogas outlet (9) and having a carbon dioxide outlet (13) and a carbon dioxide reduced biogas outlet (11);
  the at least one biomass pre-treatment reactor (2) being provided with a steam inlet connected to a steam source, and the at least one biomass pre-treatment reactor (2) being adapted to perform thermal hydrolysis at a temperature of 140-220° C., at saturation pressure; and
  the at least one digestion tank (3) being adapted to subject the pre-treated biomass material to an anaerobic digestion at a pH in a range of 7.5 to 8.5 thereby providing a digestate; characterised in that:
  a magnesium ion source inlet is arranged to add a magnesium ion source (4) to the biomass before introduction of the pre-treated biomass into the biomass digestion tank (3); and
  in that the carbon dioxide reduced biogas outlet (11) of the carbon dioxide separation device (10) is connected to a produced biogas outlet (14) of the biomass treatment plant and is connected to a carbon dioxide reduced biogas inlet (12) of the digestion tank (3) for partial re-introduction of obtained carbon dioxide reduced biogas to the digestion tank.

DETAILED DESCRIPTION OF THE INVENTION

Figure 1:
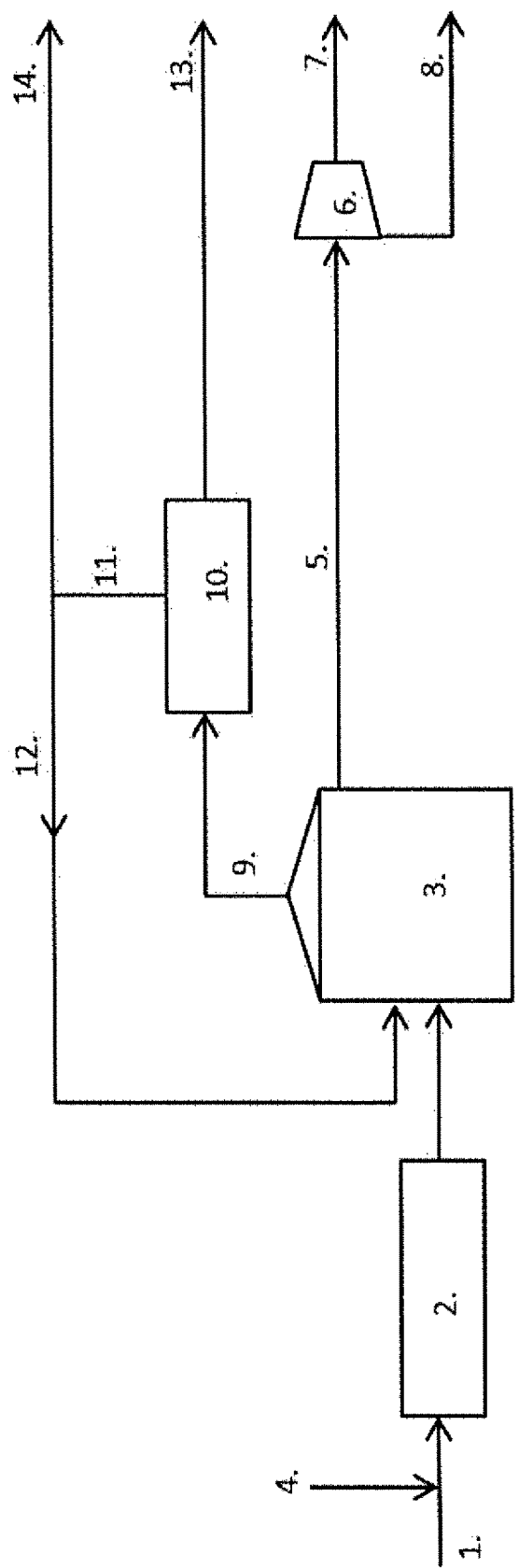
FIG. 1 is a schematic diagram of a method and biomass treatment plant according to the invention where a magnesium ion source is added prior to a thermal hydrolysis step and the pH during the digestion is controlled by removal of biogas and partially re-introducing carbon dioxide reduced biogas to the digester.

The method of the present invention allows for phosphate recovery simultaneously with digesting biomass to obtain digestion products like biogas together with a solid or semi-solid digestate product usable for e.g. soil conditioning. The phosphate is mainly recovered as MAP forming an integral part of the solid or semi-solid digestate product, which may be used directly as a soil conditioner and/or fertilizer for agricultural purposes. Typically the phosphate is recovered as MAP, or hydrates thereof, as an integral part of a solid or semi-solid digestate product.

The method of the present invention specifically recover phosphate in the form of MAP included in a re-usable solid or semi-solid digestate product. In embodiments of the invention where a dewatering of the digestate product is performed the obtained liquid waste fraction have a significantly reduced phosphate content and may be processed further without any additional phosphate reducing procedures. The present invention thereby differs from the majority of known processes for removal, reduction or recovery of phosphate as these processes typically rely on a precipitation of MAP from a wastewater effluent fraction, i.e. a recovery of substantially pure MAP from a liquid fraction, after an initial removal of the solid or semi-solid waste fraction. Due to the specific combination of method steps the method of the present invention provides a solid or semi-solid digestate product of value as soil conditioner or fertilizer instead of a solid or semi-solid-waste fraction typically requiring disposal.

The biomass material chosen for the method of the present invention may be any biomass material like e.g. straw, wood, fibres, baits, paper pulp, slurry, household waste, industrial or municipal sludge, by-products from gardening, agriculture, forestry and timber industry or other similar materials applicable in the production of biogas.

According to one embodiment of the invention, the biomass material introduced to the process is selected from the group consisting of straw, wood, fibres, baits, paper pulp, slurry, household waste, by-products from gardening, agriculture, forestry and timber industry. The present invention is especially suitable for the recovery of phosphate from the process flow of processes treating biomass material, such as e.g., straw, wood or fibers. In a preferred embodiment of the invention, the biomass material is selected from the group consisting of straw, wood, fibres and by-products from gardening, agriculture, forestry and timber industry. In a further preferred embodiment, the biomass material is selected from straw, wood and fibres. In an even further preferred embodiment the biomass material is straw.

Known methods for production of $CO_2$-neutral fuels based on biomass such e.g. organic waste often include one or more pre-treatment step employing some kind of Thermal Hydrolysis Process (THP) wherein the pre-treatment is followed by an anaerobic digestion. By the term THP is meant a thermal hydrolysis optionally followed by subsequent pre-treatment steps like oxidation and/or steam explosion.

In the method of the present invention the pre-treatment is based on a step of thermal hydrolysis performed in one or more reactor(s) using a combination of high temperature and high pressure to disintegrate the cellular structure of the organic material in the biomass and to break down high molecular weight organic compounds into smaller molecules.

The method of the invention takes advantage of the process conditions applied in the pre-treatment steps to achieve a cascade of beneficial advantages compared to the above mentioned previously described methods. A significant characteristic of the present invention is that the addition of the magnesium ion source is performed before the pre-treated biomass enters the digestion tank. In a preferred embodiment of the method of the invention step i) of adding the magnesium ion source is performed prior to or during the thermal hydrolysis process of step ii); in a more preferred embodiment step i) is performed prior to the thermal hydrolysis process of step ii). In an alternative embodiment, step i) of adding the magnesium ion source is performed after the thermal hydrolysis or during a wet explosion of step ii).

Addition of the magnesium ion source to the pre-treated biomass material prior to the material enters the digestion tank provides for the possibility to have longer process time for the reaction related to the formation of e.g. struvite as compared to most prior art processes. Hereby giving rise to a higher output of the MAP formation.

Due to the increased temperature of 140-200° C. during the thermal hydrolysis, or any subsequent optional wet-oxidation and wet-explosion steps, the solubility of the added magnesium ion source is significantly increased, which allows for the use of cheaper and less soluble magnesium salts like $Mg(OH)_2$ and $MgO$, as opposed to $MgCl_2$. In a preferred embodiment of the invention the magnesium ion source is $MgO$ and/or $Mg(OH)_2$. The magnesium ion source may be added as $MgO$ or as $Mg(OH)_2$ or as a mixture of $MgO$ and $Mg(OH)_2$. The treated biomass material may preferably have a temperature of at least 100° C. when the magnesium ion source is added. Besides the temperature, the process time is also a factor, the longer process time where the magnesium ion source is present the better solubility is obtained, and a more efficient formation of MAP later in the process is achieved. A further advantage by adding the magnesium ion source prior to the thermal hydrolysis step, e.g. in the form of $MgO$, is a reduction in energy needed to reach the appropriate temperature for the thermal hydrolysis. Due to the exothermic nature of the process heat is created and the need far heating by e.g. indirect or direct steam injection is reduced.

The formation of MAP (struvite) may already begin before the process flow enters the digestion tank, but will mainly take place during digestion. This results in the MAP, or hydrates thereof, being an integral part of the solid or semi-solid fraction of the digestate product from the digestion tank. Hereby, this solid or semi-solid fraction including the MAP is easily handled and useful as, a fertilizer product in the field of agriculture.

The method according to the invention is not dependent on a separate process equipment for MAP crystallization and/or separation. However, as the recovery of phosphate according, to the invention is highly efficient there may be instances where the phosphate content of the solid or semi-solid digestate product is actually too high for use as a fertilizer or soil conditioner. Different countries or geographical regions have different legislation as to the allowable phosphor content in fertilizers. Accordingly, the method of the invention comprises an optional step v) of reducing the phosphate concentration in the digestion tank by subjecting a sub quantity of the digestate to a phosphate removing treatment and re-introducing any remaining semi-solids into the digestion tank. If found necessary due to legislation, or for instance a very high phosphate content in available biomass, the phosphate content may be more or less reduced during the digestion process, without the need for subjecting the entire process stream to a time consuming and costly MAP crystallization and/separation procedure. Additionally, it is possible to regulate the phosphate content, as MAP or hydrates thereof, in the final digestate product avoiding a scenario where large quantities of digestate product (i.e. dewatered digestate) have to be deposited instead of reused as valuable fertilizer. In one embodiment of the invention step v) is present, i.e. mandatory.

Additionally, in embodiments of the invention where step v) is present, the MAP content of the solid or semi-solid digestate product from the digestion tank may be controlled by measuring the phosphate or phosphorous content (e.g. a orthophosphate test or a total phosphorous test) in the digestion tank and regulating the flow to the MAP separation device based on the measured phosphate content. In this manner, the extent to which the MAP reducing step is performed may be regulated. For instance, even when a biomass treatment plant has been established to include a MAP reducing step v), different types of biomass material may include varying amounts of phosphorous available for recovery as phosphate. Hence, in one embodiment of the method of the invention step v) is dependent on a measurement of the phosphate or phosphorous content in the digestate obtained in step iii). In a further specific embodiment of the invention where step v) is present, the extent of the MAP reduction performed in step v) is controlled by measuring the phosphate or phosphorous content in the digestate obtained in, step iii).

The formation of scale often caused by a high phosphate content in liquid phase of waste products has caused problems in pumps, pipes and reactors. The process according to the present invention avoids or minimizes the scaling problems in the different process equipment because the formation of struvite mainly takes place in the digestion tank, which results in the struvite being an integral part of the solid or non-liquid fraction of the digestate product from the digestion tank.

During the pre-treatment steps biomass is hydrolyzed and degraded, the resulting pre-treated biomass will normally be acidic with a pH in a range of about 4-6. The acidic pH thereby hinders formation of MAP to any large extend. However, the pH may depend on the specific biomass being treated, and the pH during the pre-treatment (step ii) herein) may preferably be kept below pH 7.0, preferably below 6.5, such as e.g. below 6.0, in order to avoid excessive formation of MAP prior to entry of the pre-treated biomass into the digestion tank.

The pre-treated biomass will furthermore have a high temperature (e.g. above 100° C.) and be characterized by a relatively high dry matter content of above 10% by weight, such as e.g., above 15%, above 20%, above 25%, above 30%, or above 35%; preferably the dry matter content of the pre-treated biomass material is of above 25% by weight, such as e.g. above 30%, above 40%, above 45%, or above 50%. Preferably the dry matter content of the pre-treated biomass material prior to the digestion step is in a range of 25% to 50% by weight.

The thermal hydrolysis may be supplemented by a subsequent step of wet explosion performed in one or more pressure relief tank(s) where the content of the tank is disintegrated due to the quick relief of the pressure. The disintegration and splitting up of the biomass makes the following step of digestion more effective.

The biomass material introduced to the method may have a dry matter (dry solid) concentration typically of above 50%, preferably above 75% by weigh, and more preferably above 80% by weight. Depending on the applied biomass material, the method according to the invention may further comprise a dilution step prior to the thermal hydrolysis.

The focus of the present invention is how to recover phosphate from pre-treated and digested biomass, namely in the form as MAP, or hydrates thereof, as an integral part of a solid or semi-solid digestate product. The pre-treatment by thermal hydrolysis and subsequent wet explosion (also named steam explosion) if included, may be performed in various ways depending on the specific material to be treated and/or the available equipment.

For instance, WO 2011/006854 describe a suitable method for thermal hydrolysis and steam explosion comprising an approximately continuously preheating step, heating and pressurizing at least two sequential reactors by the supply of steam, and leading the heated and pressurized biomass from the reactors to a first, and thereafter a second pressure relief tank, where the pressure is relieved with the help of a nozzle so that the biomass is broken up. The second pressure relief tank is under vacuum to allow steam to boil off at lower temperature. The steam from the first pressure relief tank is used in heating the preheating tank, and the steam from the second pressure relief tank is used in heating the preheating tank and/or the thermal hydrolysis reactor. The treated biomass may then be lead to a downstream installation for further treatment, such as fermentation. The described system allows for a faster cycle time and more optimal filling of the reactor volume. The details from WO 2011/006854 of each of the above steps, and how to recycle steam including how to handle non-condensing gases are incorporated herein by reference.

Alternatively, WO 00/73227 describe a suitable method and arrangement for continuous hydrolysis of biomass comprising a preheating to a temperature of approximately 100° C., a thermal treatment in a pressurized reactor which may be varied between 130 and 180° C., and an instantaneous pressure reduction (steam explosion/wet explosion). The details from WO 00/73227 of each of the above steps, and how to recycle steam/sludge and the use of heat exchangers are incorporated herein by reference.

Additionally, WO 96/09882 describe a suitable method and apparatus for hydrolysis, wherein a mixture of preheated organic material and optionally water is fed to a reactor and heated, by steam recycled from a subsequent reactor having a higher pressure. After the pressure in the subsequent reactor is reduced further, the material is transferred by means of the pressure difference or with the aid of a pump. The temperature in the first and subsequent reactors are typically 120-150° C. The treated mass is thereafter subjected to a steam explosion by transferring to further reactor. The method is described as being simpler due to the direct use of steam, allowing for simpler equipment and less maintenance problems. The details from WO 96/09882 of each of the above steps, and how to regulate pressure and temperature are incorporated herein by reference.

Further details of the preferred pre-treatment steps as well as the digestion are given below:

Thermal Hydrolysis

The method of the present invention includes a pre-treatment, comprising at least a step of thermal hydrolysis at a temperature of 140-220° C., at saturation pressure. The biomass and/or organic waste material and—if applicable—magnesium ion source is introduced to a reactor, where the material is mixed and heated with direct or indirect steam to 140-220° C., preferably 140-200° C., more preferably 150-190° C., even more preferably 160-180° C. and most preferably 170° C., at saturation pressure. When the desired temperature and the desired pressure have been reached, the material may be maintained under these conditions for 5-30 min, preferably 10-25 min, more preferably 10-20 min and most preferably 15-20 min.

Different countries or geographical regions have different legislation as to requirements for sterilization or heat-treatment of a digestate product prior to using it as e.g. soil-conditioner or fertilizer. These requirements may typically depend on the applied biomass material; for instance when the biomass material includes slaughterhouse waste, sludge, manure, biosolids, biowaste or waste streams, there may typically be a requirement for sterilization to avoid contamination of farmland with certain types of undesired or even harmful microorganisms like *E. coli*, Enterococcaceae and *Salmonella*. The legislative demands for a full sterilization typically require a heat treatment at ≥133° C. for 20 minutes, where an increased temperature allows for a reduced treatment time.

Besides the herein-above described main purpose of subjecting the biomass material to hydrolysis and degradation to facilitate biogas formation, the pre-treatment is further used to minimize the presence of undesirable microorganisms and facilitate that the end product in form of a solid or semi-solid digestate product may be used directly on e.g. farmland as soil-conditioner or fertilizer. In this manner, the MAP included in the digestate product is recovered and returned to the earth instead of ending up in waste water causing harm to the environment. Depending on the applied biomass material a sterilization may or may not be required, the thermal hydrolysis of the present invention may therefore in general be at a temperature of 140-220° C. for 5-60 minutes at saturation pressure. In embodiments of the invention requiring a sterilization, the thermal hydrolysis is preferably at a temperature of 140-180° C. for 20-40 minutes, and more preferably at a temperature of 140-165° C. for 20-30 minutes, at saturation pressure. The skilled person will know that sterilization may also be obtained at temperatures above 140° C. for shorter time intervals than 20 minutes, i.e. the higher the temperature the shorter the required time interval.

Accordingly, in specific embodiments of the invention where the biomass material introduced to the process includes one or more biomass materials selected from industrial waste, such as e.g. slaughterhouse waste, industrial sludge, or municipal sludge agricultural waste, such as e.g. manure; biosolids; biowaste; and waste streams, the conditions for pre-treatment by thermal hydrolysis are selected to ensure sterilization of the digestate product.

In one specific embodiment of the invention, the thermal hydrolysis is performed at a temperature of 140° C.-220° C., and maintained for 5-30 minutes, followed by a wet explosion carried out by means of reducing the pressure from 5-35 bar to atmospheric pressure or less.

The method may further include a pre-cooling step after the thermal hydrolysis and prior to entry of the pre-treated material into the digestion tank.

Wet Explosion

The thermally hydrolysed and optionally oxidized material may then further be led to one or more flash tank(s), at which the pressure is reduced from at least 5 bar, preferably from 5-35 bar, more preferably from 15-35 bar, to approximately 1 bar or less, i.e. atmospheric pressure or less than atmospheric pressure. In some instances, there may be a reduced pressure in a first or a further flash tank to facilitate the transfer of biomass into the tank, in such cases the pressure drop is to less than 1 bar. During this optional wet explosion most cell structures are disintegrated. Immediately after the wet explosion the temperature of the oxidized material is typically in the range of 95-120° C., preferably 95-110° C., more preferably in the range of 100-110° C., and most preferably in the range of 100-107° C., rendering the material sterile.

A wet explosion may take place in one pressure relief tank or sequentially in two or more pressure relief tanks. The term 'flash tank' and the term 'pressure relief tank' are used interchangeable herein.

Given the temperatures prevalent during a wet explosion step, the magnesium ion source may also be added to the process flow before said flow enters the wet explosion or during the wet explosion, which will in principle give rise to a number of the same benefits as those described above for processes wherein the magnesium ion source is added to the biomass entering the thermal hydrolysis step.

In a specific embodiment of the invention the pre-treatment (i.e. including at least a step of thermal hydrolysis) further comprises a wet-explosion, wherein the pressure is reduced from at least 5 bar to 1 bar or less, after said thermal hydrolysis. In embodiments of the method of the invention including a wet explosion, the step of adding the magnesium ion source may be performed after the thermal hydrolysis or during the wet explosion.

Oxidation

After termination of the thermal hydrolysis, but prior to an optional wet explosion, the pre-treatment may optionally comprise a further step of a wet-oxidation. The preferred wet-oxidation may be performed by adding an appropriate oxidizing agent to the material. The oxidizing agent may preferably be oxygen, hydrogen peroxide or air, in an amount that may depend on the content of lignin and that typically corresponds to 2-20% of the COD (chemical oxygen demand) content of the material, preferably 3-19%, more preferably 5-17%, such as preferably 7-16%, more preferably 8-15%, such as preferably 9-14%, more preferably 10-13% and determined by the pressure development in the reactor.

Pressure and temperature may be increased in connection with the wet oxidation to 15-35 bar, preferably 20-35 bar, more preferably 25-35 bar and most preferably 30-35 bar and 170-210° C., preferably 180-200° C., more preferably 190-200° C. respectively. In one embodiment the oxidation is at, a pressure above the saturation pressure in the thermal hydrolysis of the previous step. When the desired pressure and the desired temperature have been reached after the addition of the oxidizing agent, these conditions may be maintained for 1-30 min, preferably 5-25 min, more preferably 10-20 min and most preferably 15-20 min. Optionally, after termination of the wet oxidation reaction the pressure of the material may be partially released to 5-10 bar, In that case, the pressure interval at which an optional subsequent wet explosion can be performed is 1-5 bar. If no partial release of pressure is performed, then the pressure interval is 1-35 bar.

When a pre-treatment is performed by combining specifically a thermal hydrolysis, a wet-oxidation and a wet explosion further significant advantages are obtained by the method of the invention. For instance, this combination of steps makes it possible to process poorly divided material having particle sizes of up to 50 cm. Additionally, the method may operate with a dry-matter concentration of up to 50% by weight without a reduction in effectivity of the pre-treatment is seen. Further details of how to perform a pre-treatment by combining thermal hydrolysis, wet-oxidation and wet-explosion can be found in WO 2006/032282, which is incorporated herein by reference.

In one specific embodiment of the invention, the method comprises a wet oxidation after the thermal hydrolysis process and prior to an optional wet explosion, the wet oxidation is performed at a pressure of 5-35 bar, and includes addition of an oxidizing agent in an amount of 2-20% of the COD (chemical oxygen demand); the wet oxidation may preferably be carried out at a pressure of 15-35 bar and a temperature of 170-210° C., maintained for 1-30 minutes.

Digestion

In the method according to the invention the pre-treated biomass material is subjected to anaerobic digestion in one or more digestion tank(s) to produce biogas and a solid or semi-solid digestate product.

Typically when a new digestion tank for either a continuous process or a batch process is to be set-up, there, may be performed an inoculation with already processed material from an existing facility to start the anaerobic digestion.

The digestion step may employ any microorganisms capable of degrading the components of the hydrolysed biomass material to biogas. As is well known to the skilled person within the field, these microorganisms may e.g. be suitable for mesophilic digestion between 20 to 45° C., or more specifically between 30 to 38° C., where mesophiles are the primary microorganism present; or e.g. be suitable for thermophilic digestion between 49 to 70° C., or more specifically 49 to 57° C., where thermophiles are the primary microorganisms present.

Digestion tanks of any suitable, known type may be employed in performing the anaerobic digestion step included in the method according to the invention. Typically a Continuously Stirred Tank Reactor may be used, or similar suitable digestion tanks adapted with a mixing system. Typically the digestion of the present invention may be performed as a continuous process. However, more than one digestions tanks may be included in the method and treatment plant according to the invention to provide a larger capacity, such further digestion tanks may be connected in series or in parallel. In a preferred embodiment of the invention two or more digestion tanks are in, parallel operation. Typical Hydraulic Retention Times (HRT) for processes according to the present invention are 10-20 days, preferably below 18 days and more preferably 11-15 days.

Formation of MAP is dependent on pH during both the pre-treatment and the latter digestion in the digestion tank. The formation of MAP increases with increasing pH. Typically a pH value above 7.0 may increase the MAP formation, the pH value during MAP formation may preferably be of at least 7.5, such as e.g., in a pH range of 7.5-9.0 or 7.5-8.5, and more preferably a pH of at least 7.9, such as e.g., in a pH range of 7.9-9.0 or 7.9-8.5. Accordingly, in the method of the present invention the pre-treated biomass material is subjected to a digestion in the digestion tank at a pH in a range of 7.5 to 8.5; in a preferred embodiment of the invention the pH in the digestion tank is in a range of 7.5 to 83; in a more preferred embodiment in a range of 7.9 to 8.3.

During the digestion step the pre-treated biomass material is converted, and for instance proteins and other nitrogen containing material releases ammonia whereby the pH of the digestate increases. Due to the thermal hydrolysis pre-treatment, the material has a reduced viscosity allowing for a higher feed rate to the digester, and further allows for an increased organic conversion in the digester. The higher feed rate and the better organic conversion the more ammonia is released and the higher is the pH of the digester. As the volume of the digestate in the digestion tank is significantly larger than the volume added thereto from the pre-treatment step, the digestate has a certain buffer capacity so that the slightly more acidic feed from the pre-treatment typically will not affect the pH of the digestate to any significant extend. In the present invention it is however desirable to have a higher pH in the digestion tank than is usually in traditional digestion tanks. Furthermore, the pH of the pre-treated material may depend on the specific biomass used, and any pH effect on the digestate may further depend on the feed rate. The pH of the present method may therefore be controlled by use of the biogas product, as is further described below.

During the digestion step, the biogas produced may be continuously removed from the digestion tank. The directly obtained biogas will typically comprise methane, carbon dioxide and hydrogen sulphide as the major products. In the method according to the invention the ratio between methane and carbon dioxide is typically 60:40.

The present inventors have found that the pH value in the digestion tank may be controlled to favor formation of MAP by changing the equilibrium of carbon dioxide formed during the digestion. In prior art methods, there are typically added alkaline agents at some point during the process in order to increase the pH value and induce MAP formation. As also described in the background section, carbon dioxide has in one case, been added to lower pH and thereby hinder scaling in the process equipment, and subsequently removed from the wastewater by a gas stripper column to increase pH. In the method of the present invention the pH of the digestion tank is controlled by removing carbon dioxide from the produced biogas. In order to drive further carbon dioxide out of the liquid or semi-solid digestate the removed biogas is subjected to a carbon dioxide separation. This separation may be effected by any of the methods routinely applied for carbon dioxide separation in the context of industrial processes. By partially re-introducing the carbon dioxide reduced biogas, i.e. methane rich gas, into the digestion tank, the partial pressure of methane is increased and further carbon dioxide is out gassed from the liquid or semi-solid digestate which allows it to be removed. The more carbon dioxide that is removed the higher pH value. In this manner the pH may be regulated by use of the inherent components of the biogas produced in the digestion tank. No chemicals are added to the process stream and no extra external gas stripping column or external gas scrubbing is needed to out gas the carbon dioxide.

By the term "partially" re-introducing the carbon dioxide reduced biogas, is meant re-introducing a sub quantity of the carbon dioxide reduced biogas, where the quantity may be larger or smaller depending on the pH value of the digestate in the digestion tank. For instance after having re-introduced a certain quantity of the carbon dioxide reduced biogas and therefor stripping the digestion tank of further carbon dioxide and obtaining the desired pH value, the re-introduced quantity may be reduced to near zero until an adjustment of the pH is again required.

In some embodiments of the present invention the MAP concentration in the digestion tank is reduced by subjecting a sub quantity of the digestate to a MAP separation treatment and thereafter re-introducing any remaining solids or semi-solids into the digestion tank. The MAP separation may for instance be done by a cyclone or centrifuge. In a specific embodiment of the method of the invention the optional step of reducing the MAP concentration in the digestion tank is present in the method. MAP separated from a sub-quantity of the digestate in this manner, may thereafter be subjected to further purification to remove e.g. undesired digestate particles. Accordingly, in a specific embodiment of the method where the MAP reduction step is present, the method further comprises a purification of the separated MAP. This may for instance be desirable when the thus separated MAP is to be used in a commercial fertilizer product. Typically a purification may be performed by rinsing the separated MAP with water.

Dewatering

The digestate from the digestion tank may further be subjected to a separation by dewatering to obtain the solid or semi-solid digestate product. A dewatering at this stage of the process may performed by any well-known method, such as e.g. by a centrifuge, a decanter centrifuge, belt press, filter press, screw press or similar system.

Typically, dewatering of pre-treated and/or digested biomass material may require the addition of coagulation and/or flocculation agents, like e.g. polyacrylamide-based polymers (organic polymers, dry powder polymers, emulsion/liquid polymers), to obtain a sufficient particle separation and sludge dewatering. It is well known that phosphate ions in the sludge and wastewater will stabilize the formation of hydrogels and hence increase the water absorption capacity of the treated biomass. In this manner phosphate decreases the dewatering efficiency and may give rise to lower dry matter content in waste products (e.g. digestate products) and hence the need for increased use of coagulation and/or flocculation agents. The present invention reduces or eliminates the need for use of coagulation and/or flocculation agents and at the same time increases the dewatering efficiency as the phosphate ions are precipitated as MAP during the digestion process Accordingly, the dry matter content obtainable in the solid or semi-solid digestate product after de-watering of the directly obtained digestate from the digestion tank will be higher than in standard processes, due to the better separation of water from the process flow.

In a preferred embodiment of the invention, the dry-matter content of the solid or semi-solid digestate product incorporating the recovered MAP is at least as high as in standard processes. In cases where the dry-matter content of the digestate is less than in standard processes, it is especially preferred to subject the digestate to a dewatering step to obtain the solid or semi-solid digestate product including the recovered MAP as an integral part.

Fertilizer and Soil Conditioner

In a second aspect, the present invention relates to the use of a solid or semi-solid digestate product from a method according to the present invention as soil conditioner and/or fertilizer. As described herein elsewhere, the method of the present invention provides the means for reducing the MAP content in the solid or semi-solid digestate product in order to meet, any legislative requirements of a maximum allowable phosphate content. In a preferred embodiment the solid or semi-solid digestate product is used as a fertilizer.

An alternative aspect, relates to use of the solid or semi-solid digestate product from a method according to the present invention for the manufacture of a soil conditioner and/or fertilizer; preferably a fertilizer. For instance, depending on a specific agricultural purpose it may be desirable to add further specific nutrients and/or minerals prior to applying the product as soil conditioner and/or fertilizer.

Biomass Treatment Plant

The invention also relates to a device—a biomass treatment plant—accomplishing the same advantages as described for the method according to the invention.

The third aspect of the invention relates to a biomass treatment plant for production of biogas while at the same time recovering phosphate as magnesium ammonium phosphate (MAP), or hydrates thereof, from the treated biomass material, as an integral part of a solid or semi-solid digestate product.

Accordingly, the present invention relates to a biomass treatment plant for production of biogas, said biomass treatment plant including;

at least one biomass pre-treatment reactor (2) having an biomass material inlet for feeding untreated biomass material (1) and having a pre-treated biomass material outlet;

at least one digestion tank (3) having a pre-treated biomass material inlet connected to said pre-treated biomass material outlet and having a biogas outlet (9) and at least one digestate product outlet (5) for the digestate product including as an integral part recovered magnesium ammonium phosphate (MAP);

a carbon dioxide separation device (10) having a biogas inlet connected to said biogas outlet (9) and having a carbon dioxide outlet (13) and a carbon dioxide reduced biogas outlet (11);

the at least one biomass pre-treatment reactor (2) being provided with a steam inlet connected to a steam source, and the at least one biomass pre-treatment reactor (2) being adapted to perform thermal hydrolysis at a temperature of 140-220° C., at saturation pressure; and the at least one digestion tank (3) being adapted to subject the pre-treated biomass material to an anaerobic digestion at a pH in a range of 7.5 to 8.5 thereby providing a digestate; characterised in that:

a magnesium ion source inlet is arranged to add a magnesium ion source (4) to the biomass before introduction of the pre-treated biomass into the biomass digestion tank (3); and in that the carbon dioxide reduced biogas outlet (11) of the carbon dioxide separation device (10) is connected to a produced biogas outlet (14) of the biomass treatment plant and is connected to a carbon dioxide reduced biogas inlet (12) of the digestion tank (3) for partial re-introduction of obtained carbon dioxide reduced biogas to the digestion tank.

The biomass treatment plant may have discharge outlet(s) directly from the digestion tank, i.e. digestate product outlet (5), or it may have discharge outlets via a separator (6), e.g. a dewatering device, or both via a separator and directly from the digestion tank. In one embodiment a separator (6) for separation of solids is connected to a digestion tank discharge outlet (5); the separator (6), having one outlet with increased dry matter content (8), i.e. a dewatered digestate cake outlet, and one outlet with lower dry matter content (7) i.e. a liquid phase discharge outlet, the outlet with higher dry matter content is the discharge outlet from the process incorporating the MAP as an integral part of the solid or semi-solid digestate product. The separator, preferably a dewatering device, may preferably be selected from a centrifuge, decanter centrifuge, belt thickener, belt press, filter press, a screw press or similar systems.

In a specific embodiment of the invention the biomass plant comprises a dewatering device, wherein the digestate product outlet (5) from the digestion tank (3) is connected to a dewatering device (6) having a liquid phase discharge outlet (7) and a dewatered digestate product outlet (8) for the solid or semi-solid digestate product incorporating as an integral part recovered MAP.

The biomass plant according to the invention may optionally comprise a MAP separation stage adapted for reducing the MAP concentration of the digestate in the digestion tank. Accordingly, preferred embodiments of the invention further comprises a MAP separation device (17) having a digestate inlet connected via a circulation pump (16) to a digestate outlet (15) arranged at the bottom of said digestion tank (3), said MAP separation device having a MAP rich, outlet and a MAP reduced digestate outlet (18) connected to a MAP reduced digestate inlet of the digestion tank (3), wherein the MAP rich outlet is a MAP discharge outlet. The MAP reduced digestate outlet (18) may further be connected to the MAP reduced digestate inlet of the digestion tank via a temperature control device (19). Additionally, said MAP rich outlet of the MAP separation device (17) may further be connected to a MAP purification unit (20), said MAP purification unit having a purified MAP discharge outlet (22) and an excess water outlet (21) connected to a second digestion tank inlet or alternatively connected to waste. The purification unit (20) may further be provided with a water inlet. By including the MAP purification unit (20) it is possible to control the quality of separated MAP, and when included the water inlet allows for addition of cleaning water and hence further purification.

In a specific embodiment of the invention the biomass plant comprises a MAP purification unit (20) connected to the MAP rich outlet from said MAP separation device (17), said MAP purification unit (20) having a purified MAP discharge outlet (22) and an excess water outlet (21) connected to a second digestion tank inlet or connected to waste.

In embodiments of the invention where the biomass plant or method of the invention includes a MAP separation stage as described herein above, the dewatered digestate cake (5) or (8) discharged out of the process will include relatively less MAP as opposed to plants not including such a MAP separation stage. When the process do not include a MAP separation stage, the digestion tank (3) may preferably include a mixing system. The mixing system may be included in the digestion tank (3) in the form of Continuously Stirred Tank Reactors (CSTR), or the mixing system may be chosen from any commonly known systems. When the process includes a MAP separation stage a mixing system of the digestion tank may preferably be arranged to allow for extraction of digestate including sedimented MAP from a digestate outlet arranged at the bottom of the digestion tank.

As described herein in relation to the method of the invention a reduction of MAP in the digestate may depend on the phosphate content of available biomass material or any local legislation for fertilizers. In a preferred embodiment of the invention the MAP content of the solid or semi-solid digestate product from the digestion tank is controlled by measuring the phosphate content in the digestion tank and regulating the flow to the MAP separation device based on the measured phosphate content. Accordingly, in one embodiment of the biomass treatment plant having a MAP separation device, the digestate inlet of the MAP separation device (17) is connected to the digestate outlet (15) of the digestion tank (3) via a phosphate control valve; wherein the digestion tank (3), biomass material inlet (1) or digestate product outlet (5) is provided with a phosphate sensor or sampling system; and wherein a control device is adapted to control the phosphate control valve on the basis of phosphate values measured by the phosphate sensor. Preferably the digestion tank (3) or digestate product outlet (5) may be provided with the phosphate sensor or sampling system; and more preferably the digestion tank (3).

In a specific embodiment of the biomass treatment plant the carbon dioxide reduced biogas outlet (11) of the carbon dioxide separation device (10) is connected to the carbon dioxide reduced biogas inlet of the digestion tank (3) via a control valve; wherein the digestion tank (3) is provided with a pH sensor; and wherein a control device is adapted to control the control valve on the basis of pH values measured by the pH sensor.

The magnesium ion source inlet may be arranged to add a magnesium ion source (4) to the biomass or pre-treated biomass material before introduction of the pre-treated biomass into the biomass digestion tank (3). Hence, the magnesium ion source inlet (4) may be arranged to add the magnesium ion source downstream of the biomass pre-treatment reactor(s), via an inlet to the biomass pre-treatment reactor(s) (2), or upstream of the biomass pre-treatment reactor(s) but prior to entry of the pre-treated biomass into the digestion tank(s). Preferably the magnesium ion source inlet (4) may be arranged to add the magnesium ion source downstream of the biomass pre-treatment reactor(s) or via an inlet to the biomass pre-treatment reactor(s).

In embodiments of the biomass treatment plant including at least one oxidation reactor and/or at least one pressure relief reactor the magnesium ion source inlet may further be arranged to add the magnesium ions source downstream of these reactors, via an inlet to any of these reactors or upstream of any of these reactors, but prior to entry of the pre-treated biomass into the digestion tank(s).

The herein mentioned 'pre-treatment reactor' may also be termed 'thermal hydrolysis reactor'. The pre-treated biomass material outlet of the pre-treatment reactor (2) may further be connected to a pre-cooling device (23) adapted to control the temperature of the pre-treated biomass material prior to entry into the digestion tank (3). The biomass treatment plant may further comprise at least one pressure relief reactor having a pre-treated biomass material inlet connected to the pre-treatment material outlet of the biomass pre-treatment reactor and a second biomass pre-treatment reactor outlet connected to the pre-treated biomass material inlet of the digestion tank. If present the at least one pressure relief reactor may be adapted to subject the by at least thermal hydrolysis pre-treated biomass material to a wet explosion where the pressure is reduced from at least 5 bar, e.g. from 5-35 bar, to 1 bar or less.

The biomass treatment plant may further comprise at least one oxidation reactor having a pre-treated biomass material inlet connected to the pre-treatment biomass material outlet of the biomass pre-treatment reactor and a third biomass pre-treatment reactor outlet connected to the pre-treated biomass material inlet of pressure relief reactor, if present, or to the pre-treated biomass material inlet of the digestion tank. If present the at least one oxidation reactor may be adapted to subject the by thermal hydrolysis pre-treated biomass material to a wet-oxidation at a pressure of 15-35 bar and a temperature of 170-210° C.

For large-scale equipment, it is favorable to include more than one biomass pre-treatment reactors, e.g. two, three or four biomass pre-treatment reactors, for the thermal hydrolysis pre-treatment. In this manner, it is possible to run several batches with delayed cycles, whereby both the output to the digestion tank(s) is distributed over time, as well-as the required steam input for heating the biomass pre-treatment reactors is distributed more evenly. The latter is favorable for the dimensioning of the steam production facilities and energy demand thereto. In this manner a semi-continuous flow to the digestion tank may be obtained. Additionally, a further advantage of including more than one reactors for the thermal hydrolysis pre-treatment, is the upstream advantage of an increase in continuity in the feeding of the biomass pre-treatment reactors with biomass.

The features and embodiments described herein in relation to the method of the invention applies mutatis mutandis to the device, the biomass treatment plant, according to the invention; and vice versa.

DETAILED DESCRIPTION OF THE DRAWINGS

FIG. 1 is a schematic diagram of a method and a biomass treatment plant for recovery of phosphate as MAP as an integral part of a solid or semi-solid digestate product from a digestion tank. Biomass material (1) is feed to one or more biomass pre-treatment reactor(s) (2) for thermal hydrolysis being adapted to perform thermal hydrolysis at high temperature and pressure, typically 140-220° C., at saturation pressure. A magnesium ion source inlet(4) is added to the biomass prior to entry into the biomass pre-treatment reactor (s), or alternatively to the biomass in the biomass pre-treatment reactor(s) (not shown). Steam at high pressure may then be added into the reactor(s) until a sufficient high temperature and pressure is reached (not shown). After the appropriate holding time has elapsed the now pre-treated biomass is then feed to an anaerobic digestion tank (3) for digestion at elevated pH (typically in a range of 7.5 to 8.5). The anaerobic digestion tank (3) may typically be a digestion tank with an in build mixing system, such as a continuously stirred tank reactor. The pH during digestion may be controlled by continuously removing biogas (9) from the digestion tank (3), the biogas is led to a carbon dioxide separation device (10) for separating the biogas into carbon dioxide (13) fraction and a carbon dioxide reduced biogas (11) fraction, respectively. Part of the carbon dioxide reduced biogas (12) is led back into the digestion tank (3) and the remainder of the carbon dioxide reduced biogas (15) is removed as product. Digestate (5) from the digestion tank (3) may be dewatered (6) providing a solid or semi-solid digestate product as a dewatered digestate cake (8) including as an integral part the recovered MAP, and a liquid phase or water rich discharge (7).

Figure 2:
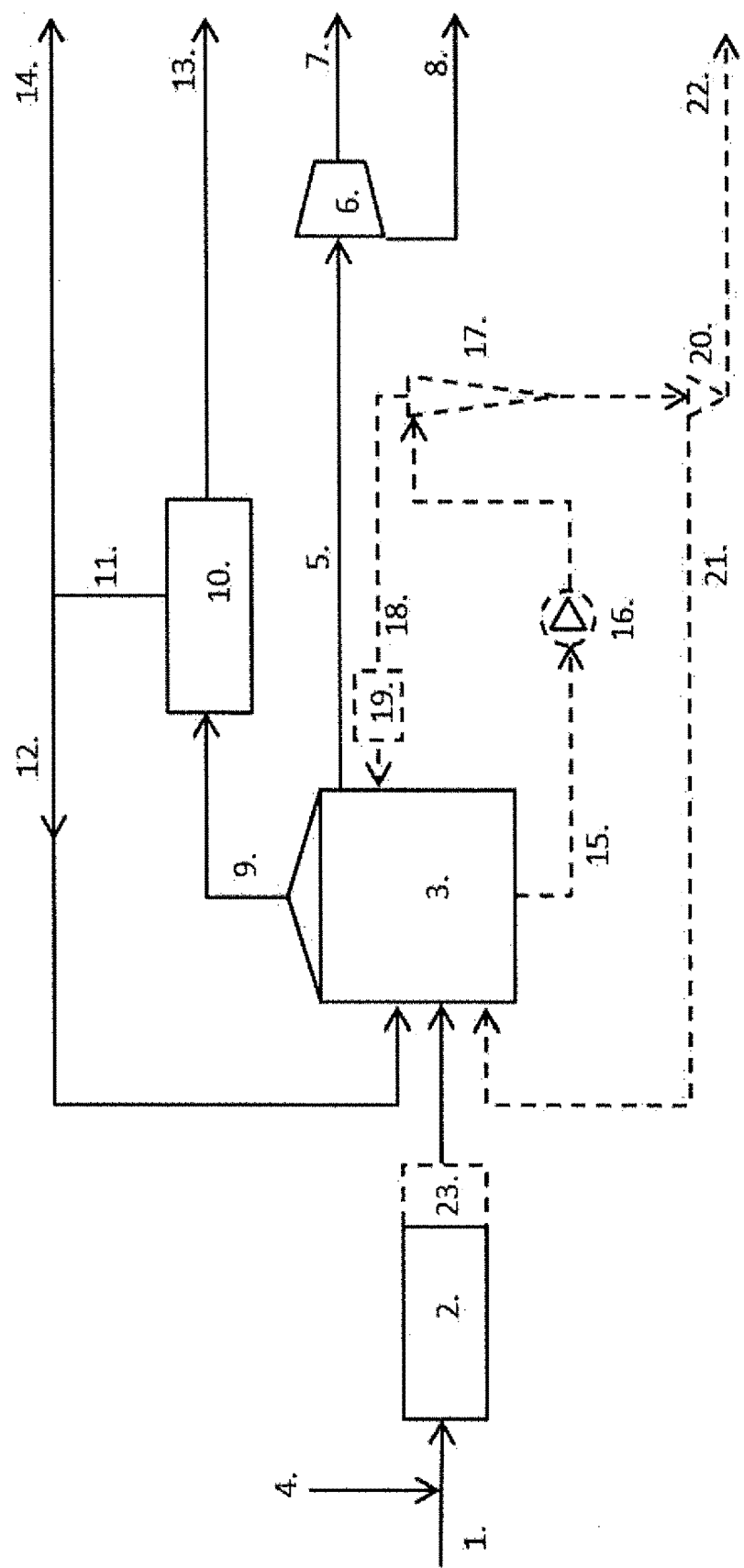
FIG. 2 is a schematic diagram of a method and biomass treatment plant according to the invention showing further optional features, including a pre-cooling of pre-treated material prior to digestion and separation of MAP for reducing the MAP concentration of the digestate.

FIG. 2 is a schematic diagram of a method and a biomass treatment plant for recovery of phosphate as MAP as an integral part of a solid or semi-solid digestate product from a digestion tank, including the optional operation of reducing the MAP concentration of the digestate and subjecting the pre-treated biomass to a pre-cooling (23). FIG. 2 is as described for FIG. 1 but includes a number of further additional optional features, one, several or all of which may be included in a method and/or treatment plant according to the present invention. Thus, FIG. 2 further shows that a sub-quantity of the digestate in the digestion tank (3) via a digestate outlet (15) arranged at the bottom of the digestion tank (3) is led to a MAP separation device (17) via a circulation pump (16), the MAP separation device (17) gives a MAP rich fraction and a MAP reduced digestate (18) fraction. The MAP reduced digestate (18) is re-introduced into the digestion tank (3), optionally via a temperature control device (19). The MAP rich fraction from the MAP separation device (17) may directly be discharged from the process as MAP product (not shown) or may be further purified in a MAP purification device (20) giving a purified MAP product (22), and an excess water discharge (21). The Excess water discharge may be directly discharged from the process (not shown) or may be reintroduced into the digestion tank (3) via a second digestion tank inlet (21). Whether or not or to what extend the optional operation of reducing the MAP concentration of the digestate is in force may be controlled by measuring the phosphate content in the digestion tank (3) or in the digestate product outlet (5) by use of a phosphate sensor or sampling system (not shown) and regulating the flow to the MAP separation device (17) based on information therefrom.

Figure 3:
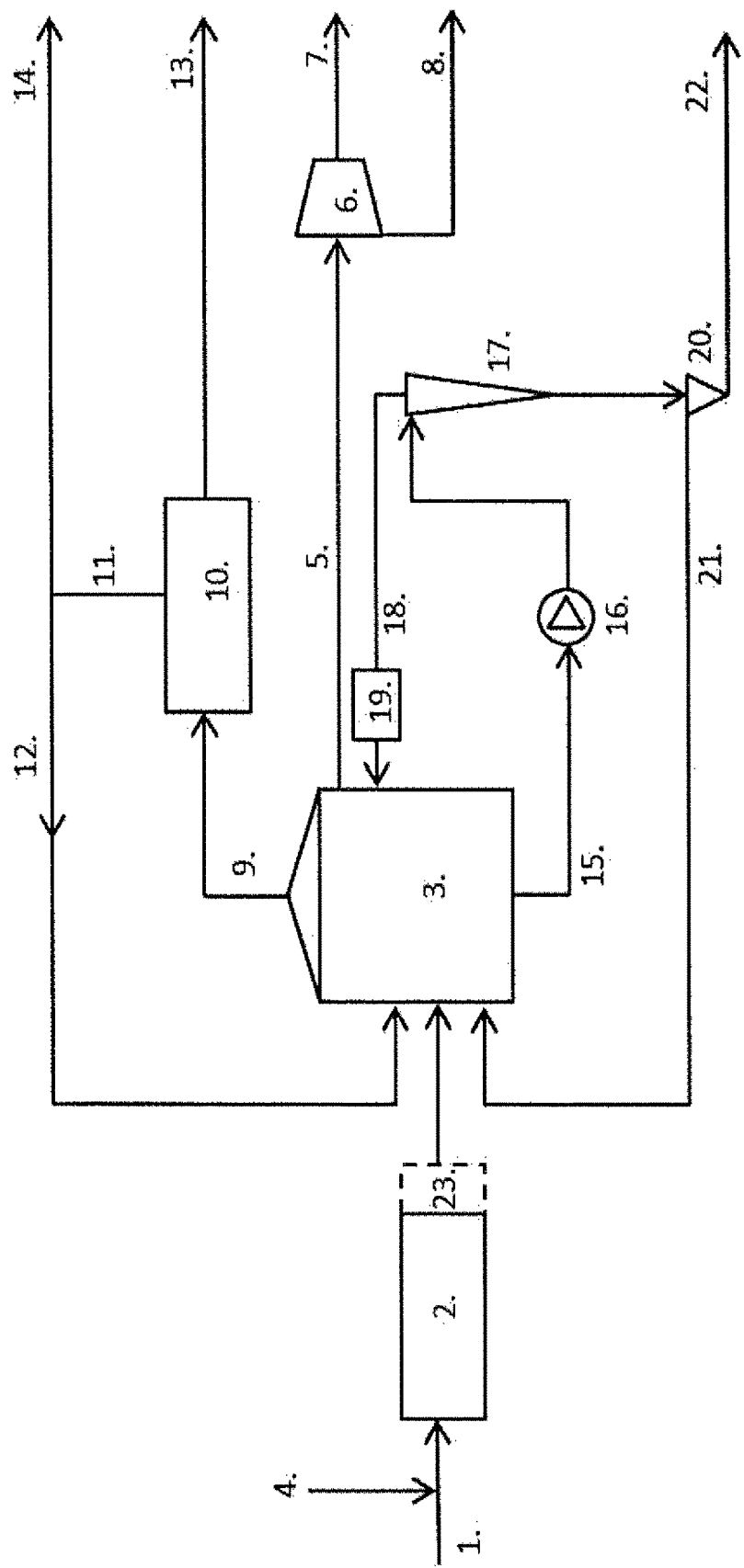
FIG. 3 is a schematic diagram of a method and biomass treatment plant according to the invention including features for reducing the MAP concentration of the digestate.

FIG. 3 is a schematic diagram of a method and a biomass treatment plant for recovery of phosphate as MAP as an integral part of a solid or semi-solid digestate product from a digestion tank. The details of FIG. 3 is as described for FIG. 2 except that the method and plant includes the operation of reducing the MAP concentration in the digestate via the MAP separation device (17) and operations relating thereto. The flow to the MAP separation device (17) from the digestion tank digestate outlet (15) may be regulated via a phosphate control device, wherein a control device is adapted to control the phosphate control valve (not shown), e.g. on the basis of phosphate values from a phosphate sensor or a phosphate sampling system.

The invention claimed is:

1. Method for recovery of phosphate from a process for treating biomass material comprising the steps of:
   i) adding a magnesium ion source to a biomass material;
   ii) subjecting the biomass material to a pre-treatment, comprising at least a step of:
      thermal hydrolysis at a temperature of 140-220° C., at saturation pressure;
   iii) transferring the pre-treated biomass material to a digestion tank and subjecting the pre-treated biomass material to an anaerobic digestion at a pH in a range of 7.5 to 8.5 thereby providing a digestate;
   iv) controlling the pH of the digestion tank by continuously removing biogas, including carbon dioxide and methane gas, and partially or fully separating the carbon dioxide from the biogas, and partially re-introducing the thereby obtained carbon dioxide reduced biogas to the digestion tank;
   v) optionally reducing a magnesium ammonium phosphate (MAP) concentration in the digestion tank by subjecting a sub quantity of the digestate to a MAP separation treatment and re-introducing any remaining solids or semi-solids into the digestion tank;
   wherein steps i) and ii) are performed prior to step iii), and wherein the phosphate is recovered as magnesium ammonium phosphate (MAP), or hydrates thereof, as an integral part of a solid or semi-solid digestate product from the digestion tank.

2. The method according to claim 1, wherein the pre-treatment of step ii) further comprises a wet-explosion, wherein the pressure is reduced from at least 5 bar to 1 bar or less, after said thermal hydrolysis.

3. The method according to claim 1, wherein step i) of adding the magnesium ion source is performed prior to, or during the thermal hydrolysis of step ii).

4. The method according to claim 1, wherein step i) of adding the magnesium ion source is performed after the thermal hydrolysis, or during the wet explosion of step ii).

5. The method according to claim 1, wherein the magnesium ion source is MgO and/or $Mg(OH)_2$.

6. The method according to claim 1, wherein step v) is present.

7. The method according to claim 1, wherein pH in the digestion tank is in a range of 7.9 to 8.3.

8. The method according to claim 1, wherein step v) further comprises a purification of the separated MAP.

9. The method according to claim 1, wherein the pH during the pre-treatment in step ii) is kept below 7.0.

10. The method according to claim 6, wherein the extent of the MAP reduction performed in step v) is controlled by measuring the phosphate or phosphorous content in the digestate obtained in step iii).

11. The method according to claim 1, wherein the digestate from step iii) is subjected to a dewatering to obtain the solid or semi-solid digestate product.

12. A biomass treatment plant for production of biogas, said biomass treatment plant including:
- at least one biomass pre-treatment reactor (2) having an biomass material inlet for feeding untreated biomass material (1) and having a pre-treated biomass material outlet;
- at least one digestion tank (3) having a pre-treated biomass material inlet connected to said pre-treated biomass material outlet and having a biogas outlet (9) and at least one digestate product outlet (5) for the digestate product including as an integral part recovered magnesium ammonium phosphate (MAP);
- a carbon dioxide separation device (10) having a biogas inlet connected to said biogas outlet (9) and having a carbon dioxide outlet (13) and a carbon dioxide reduced biogas outlet (11);
- the at least one biomass pre-treatment reactor (2) being provided with a steam inlet connected to a steam source, and the at least one biomass pre-treatment reactor (2) being adapted to perform thermal hydrolysis at a temperature of 140-220° C., at saturation pressure; and
- the at least one digestion tank (3) being adapted to subject the pre-treated biomass material to an anaerobic digestion at a pH in a range of 7.5 to 8.5 thereby providing a digestate;

characterised in that:
- a magnesium ion source inlet is arranged to add a magnesium ion source (4) to the biomass before introduction of the pre-treated biomass into the biomass digestion tank (3); and
- in that the carbon dioxide reduced biogas outlet (11) of the carbon dioxide separation device (10) is connected to a produced biogas outlet (14) of the biomass treatment plant and is connected to a carbon dioxide reduced biogas inlet (12) of the digestion tank (3) for partial re-introduction of obtained carbon dioxide reduced biogas to the digestion tank.

13. The biomass treatment plant according to claim 12, wherein the digestate product outlet (5) from the digestion tank (3) is connected to a dewatering device (6) having a liquid phase discharge outlet (7) and a dewatered digestate product outlet (8) for a solid or semi-solid digestate product incorporating as an integral part recovered MAP.

14. The biomass treatment plant according to claim 13, further comprising a MAP separation device (17) having a digestate inlet connected via a circulation pump (16) to a digestate outlet (15) arranged at the bottom of said digestion tank (3), said MAP separation device having a MAP rich outlet and a MAP reduced digestate outlet (18) connected to a MAP reduced digestate inlet of the digestion tank (3), wherein the MAP rich outlet is a MAP discharge outlet.

15. The biomass treatment plant according to claim 14, further comprising a MAP purification unit (20) connected to the MAP rich outlet from said MAP separation device (17), said MAP purification unit (20) having a purified MAP discharge outlet (22) and an excess water outlet (21) connected to a second digestion tank inlet or connected to waste.

* * * * *